United States Patent [19]

Pospisil et al.

[11] Patent Number: 5,161,969
[45] Date of Patent: Nov. 10, 1992

[54] ORTHODONTIC BRACKET

[75] Inventors: Jirina V. Pospisil, Monrovia; Joseph M. Caruso, Aquadulce; John S. Kelly, Arcadia; Jerold S. Horn, Los Angeles, all of Calif.

[73] Assignee: Minnesota Mining and Manufacturing Company, St. Paul, Minn.

[21] Appl. No.: 898,355

[22] Filed: Jun. 12, 1992

Related U.S. Application Data

[63] Continuation of Ser. No. 721,289, Jun. 26, 1991, abandoned, which is a continuation of Ser. No. 488,441, Feb. 27, 1990, abandoned, which is a continuation of Ser. No. 145,672, Jan. 14, 1988, abandoned, which is a continuation of Ser. No. 913,169, Sep. 29, 1986, abandoned.

[51] Int. Cl.⁵ .............................. A61C 3/00
[52] U.S. Cl. ........................ 433/8; 433/10
[58] Field of Search .......... 433/8, 9, 10, 11, 13, 433/15, 16, 17, 22

[56] References Cited

U.S. PATENT DOCUMENTS

| | | | |
|---|---|---|---|
| D. 290,040 | 5/1987 | Kelly | D24/16 |
| D. 291,919 | 9/1987 | Reynolds | D24/10 |
| 3,391,461 | 7/1968 | Johnson | 33/14 |
| 3,435,527 | 4/1969 | Kesling | 32/14 |
| 3,626,593 | 12/1971 | Ridgeway | 433/11 |
| 3,946,488 | 3/1976 | Miller et al. | 433/11 |
| 4,050,156 | 9/1977 | Chasanoff et al. | 32/2 |
| 4,077,126 | 3/1978 | Pletcher | 433/10 |
| 4,193,195 | 3/1980 | Merkel et al. | 433/13 |
| 4,219,617 | 8/1980 | Wallshein | 433/8 |
| 4,498,867 | 2/1985 | Kesling | 433/16 |
| 4,545,760 | 10/1985 | Forster | 433/18 |
| 4,575,337 | 3/1986 | Fujita | 433/8 |
| 4,582,487 | 4/1986 | Creekmore | 433/8 |
| 4,669,980 | 6/1987 | Degnan | 433/8 |
| 4,712,999 | 12/1987 | Rosenberg | 433/8 |
| 5,030,089 | 7/1991 | Kawaguchi | 433/8 |
| 5,044,945 | 9/1991 | Peterson | 433/8 |
| 5,067,897 | 11/1991 | Tuneberg | 433/8 |

OTHER PUBLICATIONS

Drawings "A and B".
Page 3-7 Unitek 3M Catalog.
Page 3-50 1990 Unitek 3M Catalog.

Primary Examiner—Gene Mancene
Assistant Examiner—Nicholas D. Lucchesi
Attorney, Agent, or Firm—Gary L. Griswold; Walter N. Kirn; James D. Christoff

[57] ABSTRACT

An orthodontic bracket has been designed which can be made of ceramic material. The bracket can be used for correcting Class II and Class III malocclusions without the use of a Kobiashi tie, ball hook, or power hook, which had previously been used to make such corrections. This invention, on the other hand, employs an integral hook design, which makes use of the same mechanics, but without requiring any brazing or welding of the hook to the body of the bracket.

14 Claims, 4 Drawing Sheets

ORTHODONTIC BRACKET

This is a continuation of application Ser. No. 07/721,289 filed Jun. 26, 1992, now abandoned as a continuation of Ser. No. 488,441 filed now abandoned as a continuation of Ser. No. 07/145,672 filed Jan. 14, 1988, now abandoned as a continuation of Ser. No. 06/913,169 filed Sept. 29, 1986, now abandoned

BACKGROUND OF THE INVENTION

This invention relates generally to orthodontic brackets and in particular, to brackets useful for correcting class II and Class III malocclusions.

The invention also relates, in particular to ceramic brackets.

In orthodontics, correction of Class II and Class III malocclusions is important.

Class II malocclusions are defined as malocclusions of the teeth in which the lower jaw is positioned in a patient farther back than is normal. More specifically, the mesial-buccal cusp of the lower first molar is too far distal and must be moved forward to achieve a Class I occlusion. Hence, the lower jaw must be moved forward in order to achieve a normal occlusion.

In Class III malocclusions, the lower jaw is extended in a patient forward of the normal position; and in order to correct this condition, the lower jaw must be pulled back to achieve a Class I occlusion.

In the prior art, in order to make corrections of Class II and Class III malocclusions, a variety of orthodontic appliances were employed, including ball hooks, power hooks, and Kobiashi ties. When using these appliances with brackets, either brazing or welding was required; and one of these three basic types of orthodontic appliances generally was used in order to correct the malocclusions. However, one design known as the Uni-Twin design employs an integral hook, whereby the notches are machined into the body, adjacent to the archwire slot.

Now, a new design has been developed for correction of these conditions, which design can be made and preferably is made from ceramic. This design permits the use of ceramic brackets for corrections of class II and class III malocclusions. This design can also be used to effect rotation of the teeth and consolidation of the teeth (such as is necessary when a gap is present between teeth).

SUMMARY OF THE INVENTION

An orthodontic bracket which can be made of ceramic material is provided. The bracket has the following features On the bracket body, occlusal to the archwire slot, a notch is present on the occlusal side of the bracket at a position which results in a "bifurcated single wing". Gingival to the archwire slot, at the opposite (i e., gingival) side of the bracket, two notches are present, located on opposite sides of the bracket, which form an integral hook. It is believed that a bracket having the three notches as described herein is new, useful, and unobvious.

The bracket described above also preferably features an archwire slot with a platform provided therein (described below) which is profitably used in brackets made of ceramic or of other materials.

The bracket of the invention has utility for twin bracket mechanics, whereby rotations of teeth can be achieved, up and down mechanics can be achieved, and consolidation of teeth can be achieved. The integral design of the bracket of the invention obviates the need for welding or brazing items such as ball hooks and power hooks or attaching Kobiashi ties onto brackets. If the brackets of the invention are made of ceramic, they can be dry-press molded and then machined or they can be machined entirely from rods of sintered material or grown crystalline material

DESCRIPTION OF THE PREFERRED EMBODIMENTS

FIG. 1 is a pictorial view of two brackets of the invention in a particular use on teeth, showing a condition for achieving rotation. These are shown on adjacent lower bicuspid and cuspid teeth. Also shown are ligature ties.

Figure 10:
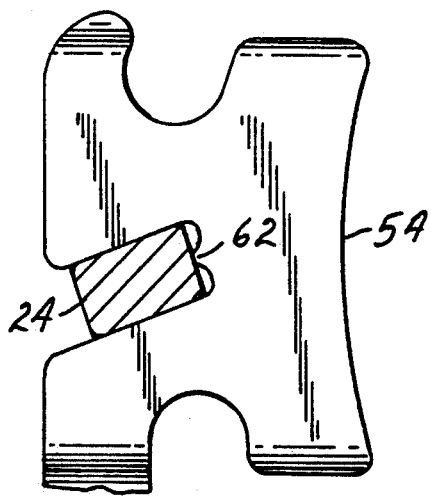
Figure 11:
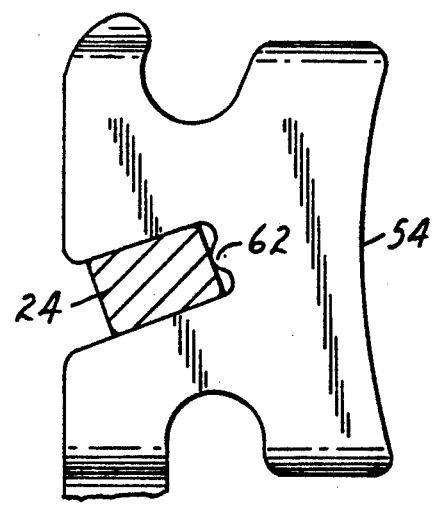
Figure 12:
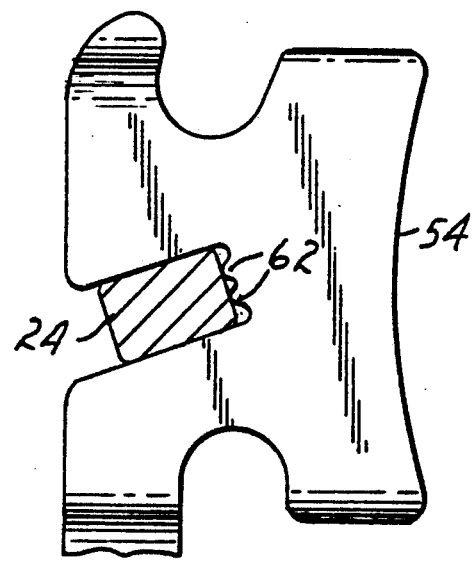

FIGS. 10, 11, and 12 show alternative embodiments of suitable shapes for the bottom of the archwire slot.

Figure 1:
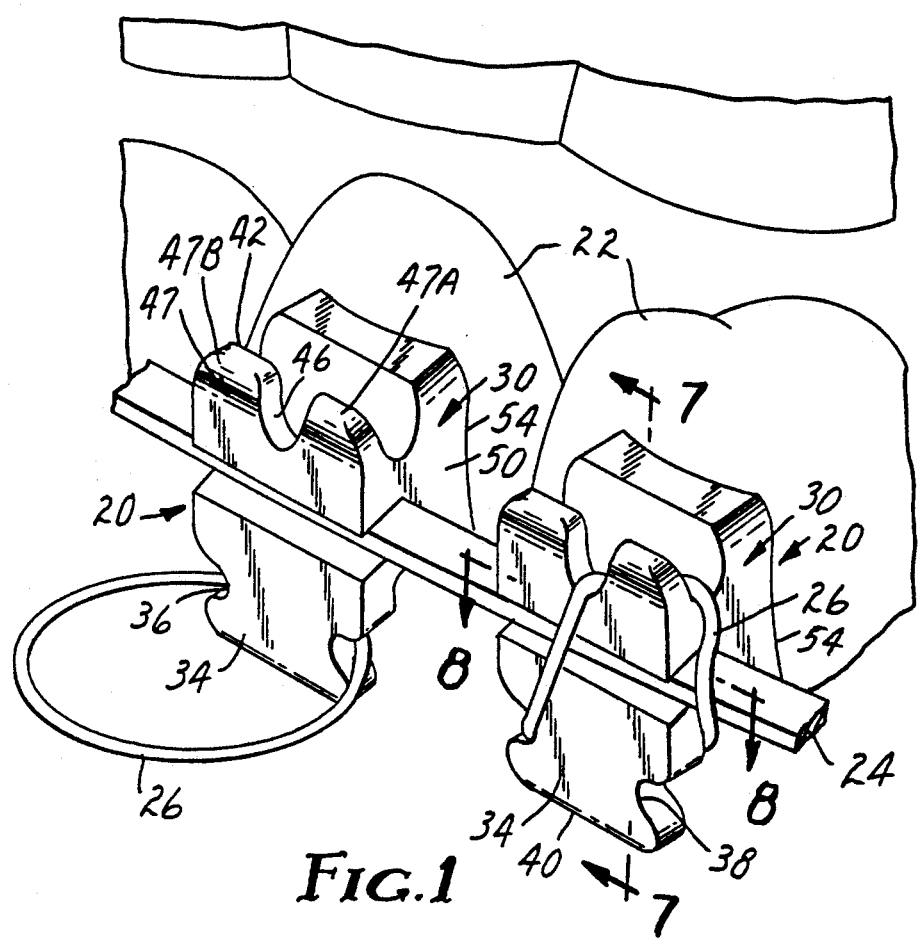
Figure 2:
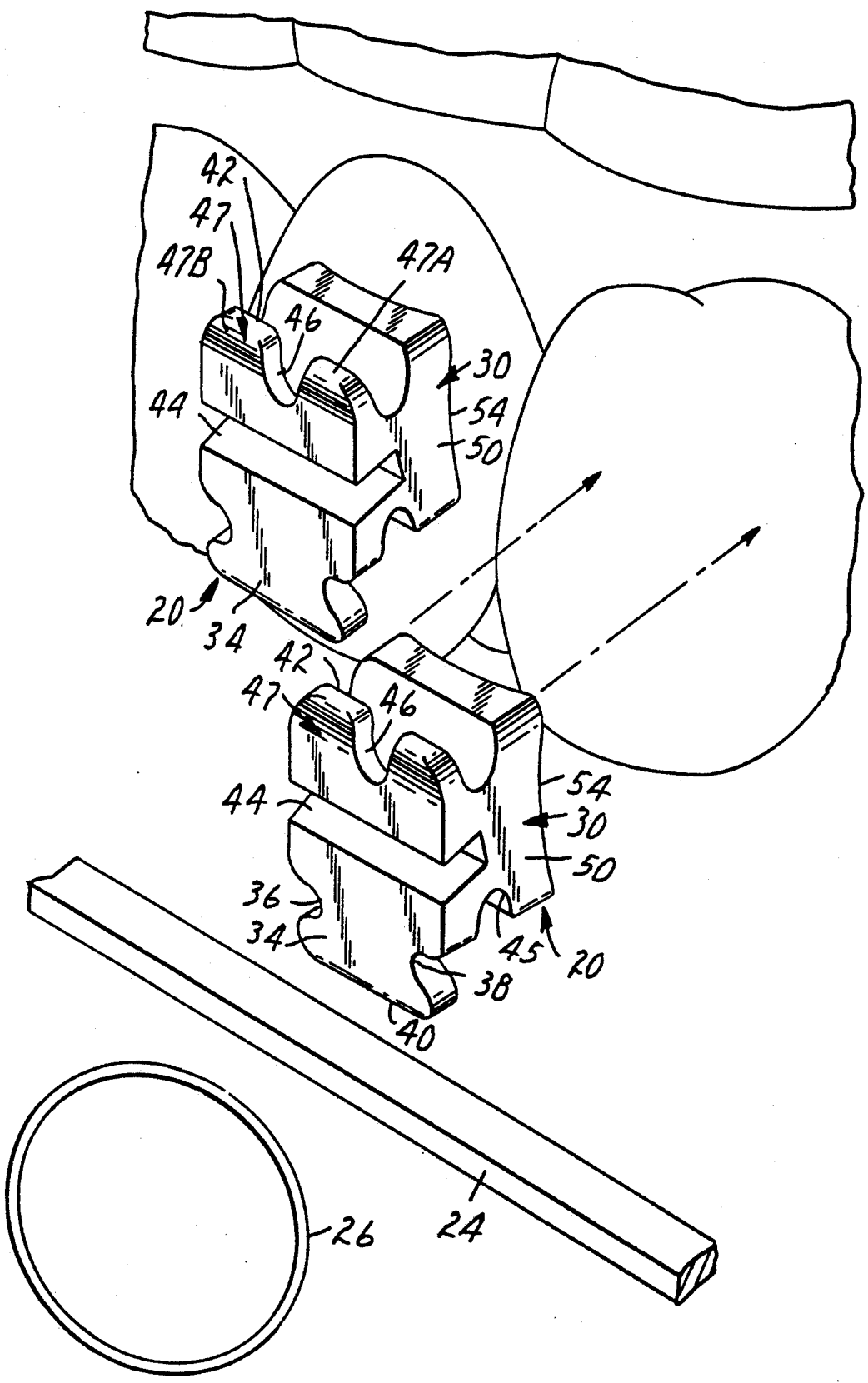
FIG. 2 is an exploded perspective view of the bracket of FIG. 1 on lower teeth, showing also an archwire which is to be positioned within the archwire slot of the bracket. A ligature tie is also shown.

In FIGS. 1 and 2, brackets of the invention referred to generally as 20 are shown in use on adjacent teeth 22. An archwire 24 is shown, together with ligatures 26.

Figures 3, 4:
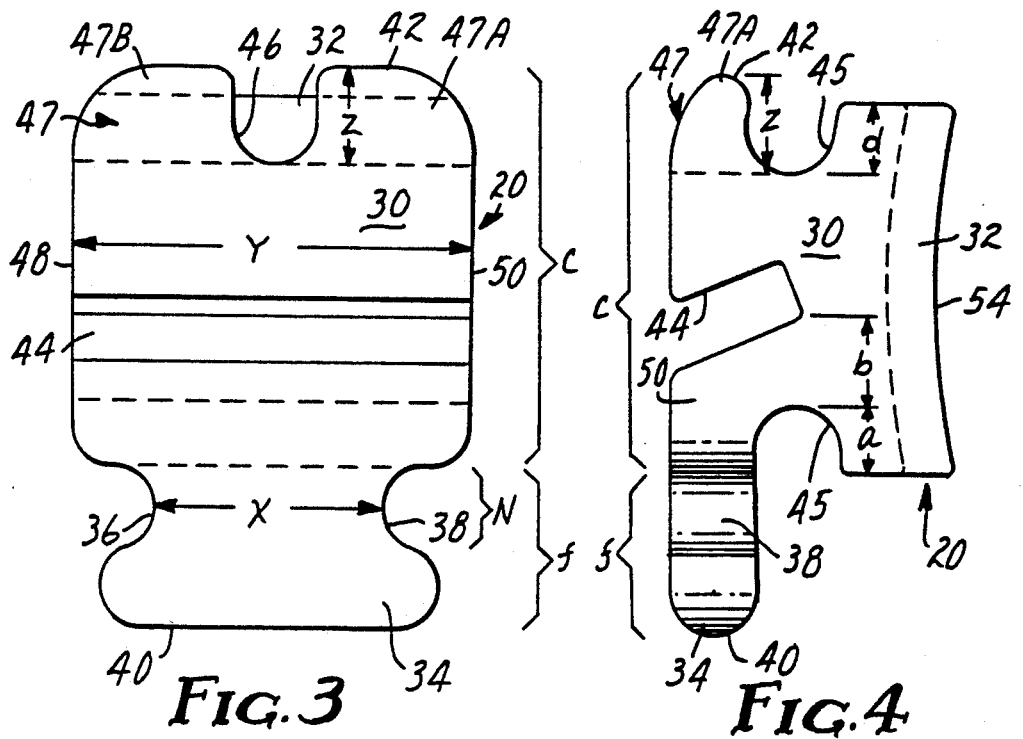
FIG. 3 is a front view of an embodiment of a bracket of the invention (having a torque and angulation according to the Roth prescription) suitable for placement onto a bicuspid tooth.
FIG. 4 is a side view of the bicuspid bracket shown in FIG. 3.
Figure 5:
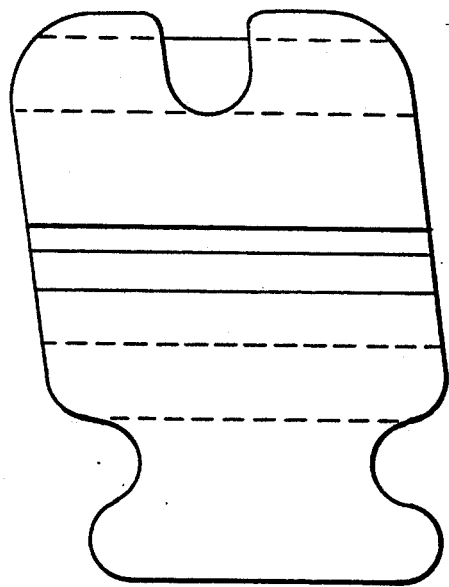
FIG. 5 is a front view of an embodiment of a bracket of the invention (also having a torque and angulation according to the Roth prescription) suitable for placement onto a cuspid tooth.

Referring to FIG. 3, in which a front view of an embodiment of a bracket of the invention (suitable for placement onto a bicuspid) is shown, this bracket exhibiting a 22° torque and a 0° angulation. Although this particular combination of torque and angulation is shown, the brackets of the invention can be made in any suitable orthodontic prescription. Currently, the Roth prescription is often used, but other prescriptions, (for example the Andrews prescription) can be used in making the orthodontic brackets of the invention.

In FIGS. 3 and 4, brackets 20 comprises a bracket body 30 which is integrally formed onto bracket base 32. Bracket body 30 features an extended integral wing 34 having a first notch 36 located therein opposite a second notch 38. Extended integral wing 34 has an extremity referred to as the gingival side 40. Bracket body 30 also has an occlusal side 42. Archwire slot 44 extends through bracket body 30 in a direction substantially parallel to gingival side 40 and occlusal side 42.

Extended integral wing 34 is machined so that notches 36 and 38 are relieved entirely through wing 34 between the gingival wing edge 40 and bracket body 30. As shown for example in FIGS. 1-3 and 5, the wing 34 has a width that is approximately the same as the width that is approximately the same as the width of the occlusal side 42 and the length of the archwire slot 44.

Bracket body 30 has a third notch 46, which is positioned on the occlusal side 42 of bracket body 30 at a position which is substantially equidistant from mesial side 48 and distal side 50. As shown in FIG. 3, third notch 46 does not extend to archwire slot 44. In effect, third notch 46 produces on occlusal side 42 a bifurcated single wing component of bracket 20. This provides utility for twin bracket mechanics, whereby either side 48 or side 50 of bracket body 30 can be rotated away from the center line of the tooth, depending upon the rotation which is desired and depending upon the placement of the ligature tie, further described below.

Notch 36 and notch 38 result in a bracket having an integral hook design. Because of this design, there is no need (as was present in the prior art) for a stud or a hook which had to be welded or brazed onto a bracket in order to achieve correction of class II and class III malocclusions. Additionally, the notches 36 and 38 result in the advantage that the ligature is easily positioned onto other brackets (i.e., it is easier to start the elastic ligature when it is desired to position the ligature around adjacent teeth, for example, than it was to position a ligature around prior art devices) And of course, the notches 36 and 38 hold the elastic ligature in position on the bracket, whereas a bracket with no such notches might not hold an elastic tie and might be unacceptable for correcting Class II and Class III malocclusions.

The distance on extended integral wing 34 between notch 36 and 38 is shown in FIG. 3 as distance "x". For strength, when the bracket 20 is made of ceramic, distance x should be relatively large as compared with the length of archwire slot 44, referred to as distance "y" in FIG. 3. Preferably, x will be at least about 50% as large as y but no more than 70% of y. Additionally, for strength, distance "z" which represents the depth of third notch 46, as shown in FIGS. 3 and 4 should be adjacent to tie wing undercut 45 and not extending through base 32.

Figure 6:
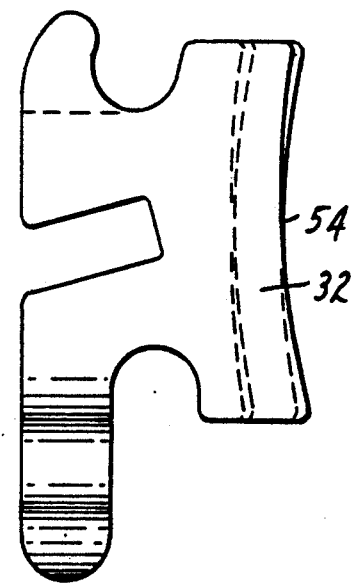
FIG. 6 is a side view of the bracket shown in FIG. 5.

As shown in FIGS. 4 and 6, bracket base 32 has a machined curvature 54 machined to fit the curvature of the tooth along the long axis of the clinical crown of the tooth. Frits 56 are shown on lower surface 54 in FIG. 7, and will be described further below.

It is pointed out that notches 36 and 38 are such that they do not continue far into bracket body 30. That is, the notched portion N does not continue far into bracket body 30, but rather only notches out a portion of extended integral wing 34. The distance f is the length of extended integral wing 34 and distance N preferably should not be greater than about 60% of f. Also, as seen on FIG. 4, distance "a" should be relatively small, and it should not be greater than distance "b".

Distance "c" shown on FIGS. 3 and 4 shows the length of bracket body 30, and distance "y" shows the width of bracket body 30.

Figure 7:
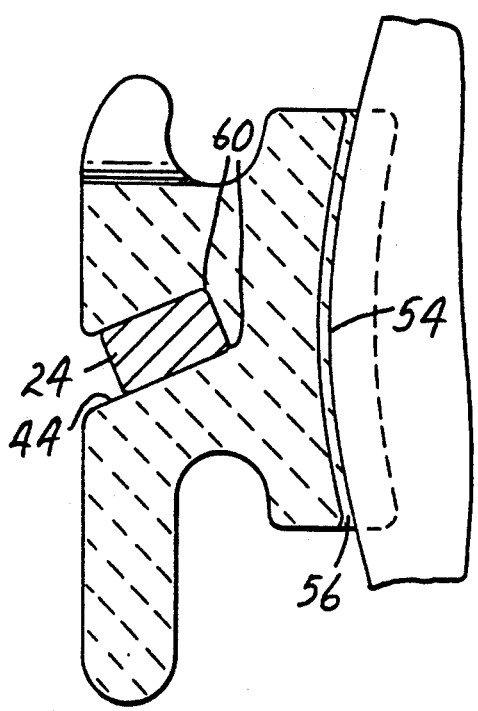
FIG. 7 is a sectional view taken along the line 7—7 of FIG. 1, showing a bracket of the invention bonded to a tooth with a bonding surface material (which can be a fritting material) present and showing an archwire within an archwire slot with rounded corners at the bottom of the slot.
Figure 8:
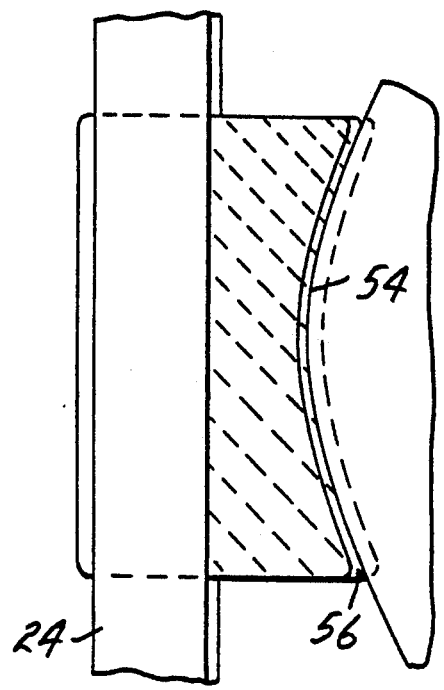
FIG. 8 is a sectional view taken along the line 8—8 of FIG. 1.

It should be noted that in FIG. 7, the archwire 24 will be generally in a horizontal position in the mouth within archwire slot 44.

Figure 9:
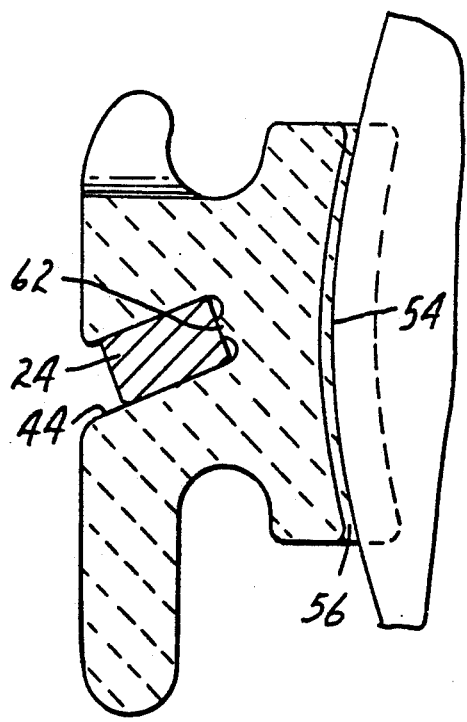
FIG. 9 is a sectional view showing a modification according to the invention of the archwire slot, the geometry of which corrects an undesirable condition which arises when the rounded corners shown in FIG. 7 are used.

Referring to FIG. 7, an important feature of archwire slot 44 is displayed. It has been found that when brackets 20 of the invention are made of ceramic, it is desirable that the lower portion of archwire slot 44 have rounded corners 60. However, rounding these corners results in an undesirable condition. When an archwire having a rectangular cross section is placed therein, high stress concentrations occur where the archwire and the slot interface It has been found that this undesirable condition can be corrected by the following design. Referring to FIG. 9, the bracket is machined such that a platform 62 for supporting the archwire 24 is produced. The platform can have a variety of shapes and a variety of ranges of total surface areas which come in contact with the archwire. As shown in FIG. 9, the preferred embodiment is a relatively wide platform portion 62.

The essential requirement for the platform 62 is as follows. The platform should be such that it positions the archwire at a level in the archwire slot which is above the level on the side walls of the slot at which the curved sections begin. This geometry allows full engagement of archwire 24 in archwire slot 44, without concentrated stresses at the bottom of archwire slot 44. As illustrated in FIG. 9, the archwire slot 44 when viewed in a direction along the longitudinal axis of the slot 44 has curved sections or corners curving inwardly toward each other along the bottom of the slot 44 from each of the opposed side walls, and the platform 62 is between the corners.

Other embodiments for suitable shapes for the bottom of archwire slot 44 are shown in FIGS. 10, 11, and 12.

In FIG. 10, an embodiment is shown, wherein platform 62 is of a smaller cross sectional area than that of the platform shown in FIG. 9.

In FIG. 11 a sine wave shape is shown as the lower surface of archwire slot 44. One and one half cycles are shown.

In FIG. 12, an alternative embodiment showing two and one half cycles of a sine wave shape is shown.

If the bracket of the invention is to be made of ceramic, it can be made by any suitable process for making ceramic brackets. One suitable procedure is to (1) prepare a mixture of ceramic powders and binder material; (2) mold the mixture; (3) eject the molded form from the mold; (4) fire the prepared form under conditions such that the composite material shrinks and the binder material vaporizes, leaving only the ceramic material in the mold; (5) then place this prepared form onto an adhesive surface (or onto a waxed surface) which can move with respect to a diamond wheel, and then machine the bracket, including the tie wing 47 and extended integral wing 34, employing a lubricant flood. The archwire slot 44 is machined in (also with lubricant flood) with a diamond wheel to remove polycrystalline material to the desired depth and shape.

Other suitable ways of providing a ceramic bracket are disclosed in U.S. Pat. No. 4,595,598 and in European Patent Application No. 85302798.5 (filed Apr. 22, 1985); and those disclosures are hereby incorporated herein by reference.

It has been found that fritting can be used to improve the bonding of such ceramic brackets to teeth. Therefore, if desired, a thin layer of fritting material can be positioned on the brackets of the present invention by any suitable means.

The brackets of this invention can be made to any suitable orthodontic prescription, employing a variety of torques and angulations. A suitable prescription of torques and angulations is of the Roth prescription. That prescription is described in the reference *Textbook of Orthodontics* by T. M. Graber.

With the Roth prescription, "straight wire finishing" is provided. That is, after the brackets are used in this prescription, no further finishing is required (except that a straight wire is placed in the mouth in order to anchor the teeth). This is further described in the Graber reference referred to above.

The orthodontic brackets of the invention can be used in any suitable manner. For example, in order to correct Class II and Class III malocclusions, first notch 36 and second notch 38 of a first bracket on a first upper tooth will be encircled with an elastic which proceeds then over the occlusal surfaces to a lower second tooth which is located adjacent to the tooth immediately below the first upper tooth, usually a molar.

In order to effect rotation of a tooth, a ligature can be shown as illustrated in FIG. 1, the ligature being positioned behind extended integral wing 34 (shown in FIG. 3), through first notch 36 and second notch 38, over archwire 24 and then under either first portion 47A or second portion 47B of tie wing 47.

If consolidation of teeth is required, elastic chain can be positioned over archwire 24 and under viewing undercuts 45, linking several orthodontic brackets together as a unit.

For effecting orthodontic corrections, the brackets of this invention are especially suitable for placement onto cuspid and bicuspid teeth.

What is claimed is:

1. An orthodontic bracket having an integrally formed gingival hook, said bracket comprising: (a) a bracket base adapted to be secured to a labial or lingual surface of a tooth; and (b) a bracket body connected to said bracket base, said bracket body having an upper surface housing an archwire slot and having mesial, distal, occlusal, and gingival sides, said archwire slot extending along said upper surface between said mesial and distal sides, wherein said bracket has an extended wing portion which is integrally connected to said bracket body, wherein said bracket includes a recess next to said bracket body and said extended wing portion for receiving a ligature, said recess including an occlusal-most surface for contact with the ligature, wherein a first notch and a second notch located within the mesial and distal extremities, respectively, of said extended integral wing portion form said integrally formed gingival hook, wherein said first notch and said second notch are spaced from said occlusal-most surface of said recess and do not extend substantially into said bracket body, and wherein said wing portion has a width that is approximately the same as the width of said occlusal side of said bracket body.

2. A bracket according to claim 1 wherein said bracket comprises ceramic material.

3. A bracket according to claim 2 wherein said archwire slot has curved corners along the bottom of said slot.

4. A bracket according to claim 3 wherein said archwire slot has a bottom surface which is a platform located at a depth within said archwire slot which is higher than the level along the sides of said slot at which the curved portions of said curved corners begin.

5. A bracket according to claim 4 wherein said platform is substantially planar.

6. A bracket according to claim 4 wherein the cross section of said platform has a lower boundary which is formed by at least two maxima of a sine wave shape.

7. A bracket according to claim 2 wherein said bracket base has adhered thereto fritting material.

8. A bracket according to claim 1 wherein said bracket consists essentially of ceramic polycrystalline alumina material.

9. A bracket according to claim 1 wherein said occlusal side of said bracket body has a third notch therein which is located substantially equidistantly from said mesial side and from said distal side of said upper surface.

10. A bracket according to claim 1 wherein said occlusal side of said bracket body has a third notch therein which is located substantially equidistantly from said mesial side and from said distal side of said upper surface.

11. An orthodontic bracket having an integral bracket body with an archwire slot having a longitudinal axis, said archwire slot when viewed in a direction along said longitudinal axis having opposed sidewalls and a bottom and corners curving inwardly toward each other along the bottom of the slot from each sidewall, wherein said archwire slot has a bottom surface which is a platform between said corners, said platform being located at a depth within said archwire slot which is higher than the level along the sides of said slot at which the curved portions of said curved corners begin.

12. A bracket according to claim 11 wherein said platform is substantially planar.

13. A bracket according to claim 11 wherein the cross section of said platform has a lower boundary which is formed by at least two maxima of a sine wave shape.

14. An orthodontic bracket having an integrally formed gingival hook, said bracket comprising: (a) a bracket base adapted to be secured to a labial or lingual surface of a tooth; and (b) a bracket body connected to said bracket base, said bracket body having an upper surface housing an elongated archwire slot and having mesial, distal, occlusal, and gingival sides, said archwire slot extending along said upper surface between said mesial and distal sides, wherein said bracket body has an extended wing portion which is integrally connected to said bracket body, wherein said bracket includes a recess next to said bracket body and said extended wing portion for receiving a ligature, said recess including an occlusal-most surface for contact with the ligature, wherein a first notch and a second notch located within the mesial and distal extremities, respectively, of said extended integral wing portion form said integrally formed gingival hook, wherein said first notch and said second notch are spaced from said occlusal-most surface of said recess, and wherein said wing portion has a width that is approximately the same as the width of said bracket base.

* * * * *

UNITED STATES PATENT AND TRADEMARK OFFICE
CERTIFICATE OF CORRECTION

PATENT NO. : 5,161,969

DATED : November 10, 1992

INVENTOR(S) : Jirina V. Pospisil, Joseph M. Caruso, John S. Kelly and Jerold S. Horn It is certified that error appears in the above-identified patent and that said Letters Patent is hereby corrected as shown below:

Col. 1, line 6, after "filed" insert -- February 27, 1990, --.

Col. 1, line 53, after "features" insert a period (.).

Col. 2, line 8, after "material" insert a period (.).

Col. 3, line 31, after "devices)" insert a period (.).

Col. 4, line 9, after "interface" insert a period (.).

Col. 5, line 26, delete "viewing" and insert -- tiewing -- therefor.

Signed and Sealed this

Twenty-first Day of December, 1993

Attest:

*Attesting Officer*

BRUCE LEHMAN

*Commissioner of Patents and Trademarks*